United States Patent
Savu et al.

(10) Patent No.: US 6,248,889 B1
(45) Date of Patent: Jun. 19, 2001

(54) PROCESS FOR CONVERTING AN ALCOHOL TO THE CORRESPONDING FLUORIDE

(75) Inventors: Patricia M. Savu, Maplewood; Daniel C. Snustad, Woodbury, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/196,512

(22) Filed: Nov. 20, 1998

(51) Int. Cl.$^7$ ............... C07D 239/02; C07C 43/15; C07C 41/09; C07C 21/18
(52) U.S. Cl. ............... 544/335; 568/607; 568/615; 568/616; 568/618; 568/623; 568/663; 570/136; 570/142
(58) Field of Search ............... 568/626, 663, 568/607, 615, 616, 618; 570/142, 144, 136; 544/335, 242

(56) References Cited

U.S. PATENT DOCUMENTS

| | | | |
|---|---|---|---|
| 2,732,398 | 1/1956 | Brice et al. | 260/503 |
| 3,419,595 | 12/1968 | Hanson | 260/456 |
| 5,474,705 | 12/1995 | Janulis et al. | 252/299.01 |
| 5,702,637 | 12/1997 | Johnson et al. | 252/299.61 |
| 5,760,255 | 6/1998 | Vorbruggen et al. | 552/502 |

FOREIGN PATENT DOCUMENTS

| | | | |
|---|---|---|---|
| WO 96/13474 | 5/1996 | (WO) | C07B/39/00 |

OTHER PUBLICATIONS

Kirk–Othmer Encyclopedia of Chemical Technology, Fourth Edition, vol. 11, pp. 562–563, John Wiley & Sons, New York, (1994). No month provided.

Bennua–Skalmowski et al., "The Reaction of Perfluorobutanesulfonyl Fluoride with Alcohols in the Presence of 4–Dialkylaminopyridines," Bull. Soc. Chim. Belg. vol. 103, No. 7–8, (1994). No month provided.

Zimmer et al., "Das Reagenz—The Reagent, Nonafluoro–1–butanesulfonyl Fluoride: More than a Fluorinating Reagent", J. prakt. Chem. 340, pp. 274–777 (1998). No month provided.

Bennua–Skalmowski et al., "A Facile Conversion of Primary or Secondary Alcohols with n–Perfluorobutanesulfonyl Fluoride/1,8–Diazabicyclo[5.4.0]undec–7–ene into their Corresponding Fluorides," Tetrahedron Letters, vol. 36, No. 15, pp. 2611–2614, (1995). No month provided.

Kiesewetter et al., "Synthesis of 16–Fluoroestrogens by Unusually Facile Fluoride Ion Displacement Reactions: Prospects for the Preparation of Fluorine–18 Labeled Estrogens," J. Org. Chem., 49, pp. 4900–4905 (1984). No month provided.

Nohira et al., "Synthesis and Mesomorphic Properties of Ferrolectric Liquid Crystals with a Fluorinated Asymmetric Frame (1)", Mot. Cryst. Liq. Cryst., vol. 180B, pp. 379–388 (1990). No month provided.

Middleton, "New Fluorinating Reagents, Dialkylaminosulfur Fluorides," J. Org. Chem., vol. 40, No. 5, pp. 574–578 (1975). No month provided.

Trott et al., 126$^{th}$ National Meeting of the American Chemical Society, pp. 42M–43M, New York, (1954)–abstract only.

Abe et al., Electrochemical Fluorination (Simons Process) as a Route to Perfluorinated Organic Compounds of Industrial Interest, Preparation, Properties, and Industrial Applications of Organofluorine Compounds, Ellis Howard, pp. 37–43 (1982). No month provided.

E.P. Hunter and S.G. Lias, Proton Affinity Evaluation, NIST Chemistry WebBook, NIST Standard Reference Database No. 69, Eds. W.G. Mallard and P.J. Linstrom, Mar. 1988 (internet address: webbook.nist.gov/cgi/cbook.cgi).

*Primary Examiner*—Rosalynd Keys
(74) *Attorney, Agent, or Firm*—Lucy C. Weiss

(57) ABSTRACT

A process for preparing a fluoride from its corresponding alcohol comprises the steps of (a) forming a mixture comprising (i) at least one fluorinated, saturated aliphatic or alicyclic sulfonyl fluoride (for example, perfluorobutanesulfonyl fluoride) and (ii) at least one primary or secondary alcohol; and (b) adding a molar excess of at least one strong, aprotic, non-nucleophilic, hindered, double bond-containing, organic base (for example, 1,8-diazabicyclo[5.4.0]undec-7-ene (DBU)) to the mixture.

28 Claims, No Drawings

PROCESS FOR CONVERTING AN ALCOHOL TO THE CORRESPONDING FLUORIDE

FIELD OF THE INVENTION

This invention relates to a process for converting a primary or secondary alcohol to its corresponding fluoride.

BACKGROUND OF THE INVENTION

Organic compounds selectively substituted with fluorine have utility as drugs, agrichemicals, medical imaging agents, and high polarization additives for ferroelectric liquid crystal compositions, as well as in many other applications. Fluorinated steroids and drugs are often more potent than their unsubstituted analogs due to increased lipophilic behavior, suppression of undesired metabolic reactions, and reduced binding to serum proteins. (See, e.g., J. A. Katzenellenbogen et al., J. Org. Chem. 49, 4900 (1984).) Chiral ferroelectric liquid crystal compounds having a fluorine atom at the chiral center exhibit larger spontaneous polarizations and greater smectic character than their hydrocarbon analogs. (See, e.g., H. Nohira et al., Mol. Cryst. Liq. Cryst. 180B, 379, 385 (1990).)

The preparation of such selectively fluorinated materials poses special difficulties due to a tendency for hydrogen fluoride elimination under the conditions conventionally used to prepare these materials. One commonly used strategy is to replace a hydroxyl group (in a starting compound) with a fluorine atom, but this is not an easy transformation since carbonium ion rearrangements and dehydration to an olefin can occur. (See, e.g., W. J. Middleton, J. Org. Chem. 40, 574 (1975).)

Such side reactions can be minimized by the use of DAST (diethylaminosulfur trifluoride) as the fluorinating reagent. DAST fluorinations can be carried out under mild conditions, making DAST more convenient to use than some other fluorination reagents such as sulfur trifluoride. (See, e.g., M. Hudlicky, *Organic Reactions*, volume 35, page 513, John Wiley and Sons, New York (1988).) However, DAST is not commercially available and is costly to produce (due, e.g., to the need for specialized preparation and handling equipment), and the yields obtained using DAST are often only moderate.

Selectively fluorinated materials have also been prepared from their hydroxyl-functional equivalents (primary and secondary alcohols) using perfluoroalkanesulfonyl fluorides and strong bases in organic solvent (as described by B. Benua-Skalmowski and H. Vorbrueggen in Tetrahedron Letters 36 (15), 2611 (1995), as well as in International Patent Publication No. WO 96/13474 (Vorbrueggen) and U.S. Pat. No. 5,760,255 (Vorbrueggen et al.)). This method has involved the use of 2 to 3 equivalents of base, with addition of the perfluoroalkanesulfonyl fluoride to a premix of alcohol and base.

However, there is a continuing need in the art for a selective fluorination process that is useful on an industrial scale. Such a process should not only be cost effective and capable of being carried out using common multipurpose industrial equipment, but should also be able to consistently provide good to excellent yields under the variable conditions commonly encountered in a factory setting.

SUMMARY OF THE INVENTION

Briefly, this invention provides an improved, industrially useful process for preparing a fluoride from its corresponding alcohol using a fluorinated sulfonyl fluoride as the source of the fluorine. The process comprises the steps of (a) forming a mixture comprising (i) at least one fluorinated, saturated aliphatic or alicyclic sulfonyl fluoride (e.g., perfluorobutanesulfonyl fluoride) and (ii) at least one primary or secondary alcohol (e.g., 6-hydroxyoctene); and (b) adding a molar excess of at least one strong, aprotic, non-nucleophilic, hindered, double bond-containing, organic base (e.g., DBU, 1,8-diazabicyclo[5.4.0]undec-7-ene) to the mixture. (As used herein, the term "strong organic base" means an organic base that is capable of enabling the formation of a sulfonate ester without substantially inducing elimination of, e.g., hydrogen fluoride or sulfonate anion.) Due to the exothermic nature of the reaction, the mixture is preferably precooled, e.g., to a temperature in the range of about −30° C. to about 0° C., prior to addition of the organic base.

It has been discovered that the process of the invention, which involves the addition of base to a premix of alcohol and sulfonyl fluoride, surprisingly provides significantly better selectivity and significantly higher yields of the desired fluoride than both the prior art sulfonyl fluoride-based method (which involves the addition of sulfonyl fluoride to a premix of base and alcohol) and the use of DAST. Furthermore, unlike the prior art sulfonyl fluoride-based method (which requires the use of 2 to 3 equivalents of base), the process of the invention consistently provides excellent yields, regardless of the size of the excess of base utilized.

As with the use of DAST, the process of the invention, when carried out using a chiral alcohol, proceeds with complete inversion of configuration at the chiral center. The process can, however, be carried out more safely than processes which utilize DAST as the fluorinating reagent, as, unlike DAST, the reactants do not fume in the open air, decompose violently at temperatures above 50° C., or burn the skin upon contact.

Furthermore, since the process of the invention utilizes fluorinated sulfonyl fluorides, rather than the higher cost diethylaminosulfur trifluoride (DAST), and since it does not require as large an excess of base as the prior art sulfonyl fluoride-based method, it provides better selectivity and higher yields of desired product (than the prior art methods) at lower raw material costs. The process of the invention therefore satisfies the need in the art for a cost effective selective fluorination process that consistently provides excellent yields under variable reaction conditions.

In another aspect, this invention also provides an improved, sulfonyl fluoride-based selective fluorination process that utilizes the conventional premix of base and alcohol but a molar excess of base of less than 2 equivalents per equivalent of alcohol.

DETAILED DESCRIPTION OF THE INVENTION

Sulfonyl fluorides suitable for use in the process of the invention are fluorinated, saturated aliphatic or alicyclic sulfonyl fluorides. A useful class of such sulfonyl fluorides can be represented by the general formula $R_fSO_2F$, where $R_f$ is selected from the group consisting of perfluorinated alkyl groups having from 1 to about 10 carbon atoms; partially-fluorinated alkyl groups having from 1 to about 10 carbon atoms; unsubstituted or perfluoroalkyl-substituted, perfluorinated cycloalkyl groups having from about 4 to about 8 carbon atoms; and unsubstituted or perfluoroalkyl-substituted, partially-fluorinated cycloalkyl groups having from about 4 to about 8 carbon atoms. Preferably, $R_f$ is a perfluorinated alkyl group.

Perfluorinated sulfonyl fluorides can be prepared by electrochemical fluorination of the corresponding hydrocarbon sulfonyl fluorides, as described in U.S. Pat. No. 2,732,398 (Brice et al.), the description of which is incorporated herein by reference. (See also P. W. Trott et al, 126$^{th}$ National Meeting of the American Chemical Society, abstract at page 42-M, New York, N.Y. (1954).) Perfluorooctanesulfonyl fluoride is also commercially available from 3M Co. under the tradename Fluorad™ fluorochemical sulfonyl fluoride FX-8. Partially-fluorinated sulfonyl fluorides can be prepared from hexafluoropropylene oxide and the ring-opened sulfur trioxide oxetane of tetrafluoroethylene, as described, e.g., in *Kirk-Othmer Encyclopedia of Chemical Technology*, Fourth Edition, Volume 11, pages 562–63, John Wiley & Sons, New York (1994).

Representative examples of sulfonyl fluorides suitable for use in the process of the invention include $CF_3SO_2F$, $C_2F_5SO_2F$, $C_4F_9SO_2F$, $C_6F_{13}SO_2F$, $C_8F_{17}SO_2F$, $C_{10}F_{21}SO_2F$, cyclo-$(C_6F_{11})SO_2F$, $C_2F_5$-cyclo-$(C_6F_{10})SO_2F$, $H(CF_2)_4SO_2F$, $H(CF_2)_8SO_2F$, and mixtures thereof. Preferably, perfluorobutanesulfonyl fluoride, perfluorohexanesulfonyl fluoride, perfluorooctanesulfonyl fluoride, and mixtures thereof are utilized, as these sulfonyl fluorides are liquids under normal conditions and can be obtained in high yields from electrochemical fluorination processes, at correspondingly low costs (see, e.g., T. Abe et al., "Electrochemical Fluorination (Simons Process) as a Route to Perfluorinated Organic Compounds of Industrial Interest," in *Preparation, Properties, and Industrial Applications of Organofluorine Compounds*, R. E. Banks (editor), page 37, Ellis Howard (1982)). Most preferably, perfluorobutanesulfonyl fluoride is utilized in the process of the invention, due to its solubility in common organic solvents and the resulting ease of organic/aqueous phase separations.

Alcohols suitable for use in the process of the invention are primary and secondary alcohols, including both monoalcohols (carbinols) and polyols. A useful class of such alcohols can be represented by the general formula $R_1R_2CH$—OH, where $R_1$ and $R_2$ are independently selected from the group consisting of branched or linear aliphatic groups, alicyclic groups, araliphatic groups, aromatic groups, hydrogen, branched or linear fluoroaliphatic groups, fluoroalicyclic groups, fluoroaraliphatic groups, and fluoroaromatic groups (preferably, aliphatic, fluoroaliphatic, araliphatic, or alicyclic; more preferably, aliphatic, fluoroaliphatic, or araliphatic). The aliphatic, alicyclic, araliphatic, fluoroaliphatic, fluoroalicyclic, and fluoroaraliphatic groups can contain catenary (in-chain) heteratoms (such as oxygen, nitrogen, or sulfur) and/or up to two olefinic double bonds. Here and throughout the specification, the prefix "fluoro-" and the term "fluorinated" are meant to include both perfluorinated and partially-fluorinated moieties or compounds.

Thus, the fluoroaliphatic groups can comprise one or more moieties selected from the group consisting of branched or linear aliphatic groups, alicyclic groups, and araliphatic groups in which any one or more of the hydrogen atoms is replaced with a fluorine atom. For example, the fluoroaliphatic groups can comprise a moiety that can be represented by the formula —D—$R_f$', where D is selected from the group consisting of a covalent bond, —O—, —$OC_rH_{2r}$—, $O(C_rH_{2r}O)_t$—$C_rH_{2r}$—, —$C_rH_{2r}$—, and —$(C_rH_{2r}O)_t$—$C_rH_{2r}$—, where r is an integer of 1 to about 20 and t is an integer of 1 to about 6; and $R_f$' is selected from the group consisting of —$(C_xF_{2x}O)_zC_yF_{2y+1}$ and —$C_qF_{2q}X$, preferably —$(C_xF_{2x}O)_zC_yF_{2y+1}$, where x is independently an integer of 1 to about 10 (preferably, 1 to about 4) for each $C_xF_{2x}O$ group, y is an integer of 1 to about 10 (preferably, 1 to about 6), z is an integer of 1 to about 10 (preferably, 1 to about 3), q is an integer of 1 to about 15, and X is selected from the group consisting of hydrogen and fluorine.

Representative examples of useful alcohols include
$CH_3CHOHCH(CH_3)_2$,
$C_6H_{11}OH$,
$C_6F_{11}CHOHCH_3$,
$C_6H_5CH_2CH_2CH_2OH$,
$C_6F_5CH_2CH_2CH_2OH$,
$C_6H_5CHOHC_6H_5$,
$C_6F_5CHOHC_6H_5$,
$CH_3OCOCH_2CHOHCH_2CH_3$,
$C_{10}H_{11}OH$ (1,2,3,4-tetrahydro-2-hydroxynaphthalene),
$CH_2=CH\ CH_2)_nCH(OH)CH_2OCH_2—(C_xF_{2x}O)_zC_yF_{2y+1}$,
$C_6H_5CH_2O(CH_2)_nCH(OH)CH_2—(C_xF_{2x}O)_zC_yF_{2y+1}$,
$CH_3C(=O)O(CH_2)_nCH(OH)CH_2OCH_2—(C_xF_{2x}O)_zC_yF_{2y+1}$,
THP—$O(CH_2)_nCH(OH)CH_2OCH_2—(C_xF_{2x}O)_zC_yF_{2y+1}$,
$C_8H_{17}—C_4H_2N_2—C_6H_4O(CH_2)_nCH(OH)CH_2OCH_2(C_xF_{2x}O)_zC_yF_{2y+1}$,
$C_7H_{15}—C_4H_2N_2—C_6H_4O(CH_2)_nCH(OH)CH_2OCH_2(C_xF_{2x}O)_zC_yF_{2y+1}$,
$C_6H_{13}—C_4H_2N_2—C_6H_4O(CH_2)_nCH(OH)CH_2OCH_2(C_xF_{2x}O)_zC_yF_{2y+1}$,
$C_9H_{17}O—C_4H_2N_2—C_6H_4O(CH_2)_nCH(OH)CH_2OCH_2(C_xF_{2x}O)_zC_yF_{2y+1}$,
$C_7H_{15}O—C_4H_2N_2—C_6H_4O(CH_2)_nCH(OH)CH_2OCH_2(C_xF_{2x}O)_zC_yF_{2y+1}$,
$C_6H_{13}O—C_4H_2N_2—C_6H_4O(CH_2)_nCH(OH)CH_2OCH_2(C_xF_{2x}O)_zC_yF_{2y+1}$,
$CH_3(CH_2)_bCH(OH)(CH_2)_mCH=CH_2$,
$CH_3(CH_2)_bCH(OH)(CH_2)_mOC(=O)CH_3$, $CH_3(CH_2)_bCH(OH)(CH_2)_mO$—THP,
$CH_3(CH_2)_bCH(OH)(CH_2)_mOCH_2C_6H_5$, thymidine, 5'-deoxythymidine, uridine, 2'-deoxyuridine, 2'-deoxy-5-(trifluoromethyl)uridine, guanosine, 2'-deoxyguanosine, adenosine, 2'-desoxyadensoine, 5'-deoxyadenosine, and mixtures thereof, where x is independently an integer of 1 to about 10 (preferably, 1 to about 4) for each $C_xF_{2x}O$ group, y is an integer of 1 to about 10 (preferably, 1 to about 6), and z is an integer of 1 to about 10 (preferably, 1 to about 3), where n and m are independently integers of one to about ten, b is an integer of zero to about 10, and THP=tetrahydropyranyl. Although the preceding representative structures are shown as racemic materials, the process of the invention can be carried out using chiral, racemic, or non-optically active carbinols. Steroidal carbinols (for example 16alpha-hydroxyestone, 3beta-hydroxycholestan, 3alpha-andostan, 16beta-hydoxy-3-[[(trifluoromethyl)sulfonyl]oxy]esta-1,3,5(10)-trien-17-one, and mixtures thereof) are also useful in the process of the invention.

Preferred alcohols include
$CH_2=CH(CH_2)_2CH(OH)CH_2OCH_2CF_2OCF_2CF_2OC_4F_9$,
$C_6H_5CH_2O(CH_2)_2CH(OH)CH_2OCH_2CF_2OCF_2CF_2OC_4F_9$,
$CH_3C(=O)O(CH_2)_2CH(OH)CH_2OCH_2CF_2OCF_2CF_2OC_4F_9$,
THP—$OCH_2CH(OH)CH_2OCH_2CF_2OCF_2CF_2OC_4F_9$,
$CH_2=CH(CH_2)_2CH(OH)CH_2OCH_2CF_2O(CF_2CF_2O)_2CF_3$,
$CH_3C(=O)O(CH_2)_2CH(OH)CH_2CH_2OCH_2CF_2O(CF_2CF_2O)_2CF_3$,
$C_6H_5CH_2O(CH_2)_2CH(OH)CH_2CH_2OCH_2CF_2O(CF_2CF_2O)_2\ CF_3$,
THP—$O(CH_2)_2CH(OH)CH_2CH_2OCH_2CF_2O(CF_2CF_2O)_2CF_3$,
$CH_2=CH(CH_2)_2CH(OH)CH_2OCH_2CF_2CF_2OC_2F_5$, $C_6H_5CH_2O(CH_2)_2CH(OH)CH_2OCH_2CF_2CF_2OC_2F_5$,
$CH_3C(=O)O(CH_2)CH(OH)CH_2OCH_2CF_2CF_2OC_2F_5$,
THP—$O(CH_2)CH(OH)CH_2OCH_2CF_2CF_2OC_2F_5$,
$C_6H_5CH_2O(CH_2)_2CH(OH)CH_2OCH_2C_7F_{15}$,
$C_6H_5CH_2O(CH_2)_2CH(OH)CH_2OCH_2C_3F_7$,
$C_8H_{17}$—$C_4H_2N_2$—$C_6H_4OCH_2CH(OH)$
  $CH_2OCH_2CF_2OCF_2CF_2OC_4F_9$,
$C_8H_{17}$—$C_4H_2N_2$—$C_6H_4OCH_2CH(OH)CH_2OCH_2CF_2O$
  $(CF_2CF_2O)_2CF_3$,
$C_8H_{17}O$—$C_4H_2N_2$—$C_6H_4OCH_2CH(OH)$
  $CH_2OCH_2CF_2CF_2OC_2F_5$,
$C_8H_{17}$—$C_4H_2N_2$—$C_6H_4OCH_2CH(OH)CH_2OCH_2C_7F_{15}$,
$CH_3CH(OH)(CH_2)_4OCH_2C_6H_5$, $CH_3CH_2CH(OH)(CH_2)_4OCH_2C_6H_5$,
$CH_3CH_2CH_2CH(OH)(CH_2)_4OCH_2C_6H_5$,
$CH_3(CH_2)_3CH(OH)(CH_2)_4OCH_2C_6H_5$, $CH_3CH_2CH(OH)$
  $(CH_2)_3CH=CH_2$, and mixtures thereof, where THP= tetrahydropyranyl.

Bases suitable for use in the process of the invention are strong, aprotic, non-nucleophilic, hindered, double bond-containing, organic bases. As used herein, the term "strong organic base" means an organic base that is capable of enabling the formation of a sulfonate ester without substantially inducing elimination of, e.g., hydrogen fluoride or sulfonate anion. Preferably, the base exhibits a gas phase proton affinity of at least about 1000 kJ/mole (more preferably, at least about 1030 kJ/mole). The term "non-nucleophilic," as used herein, means a base that does not undergo an irreversible reaction with the sulfonyl fluoride group and thereby reduce the yield of desired fluorocompound, and "hindered" refers to a base having a spatial arrangement of atoms such that displacement of a sulfonate ester group by the base is essentially prevented and does not occur. (See, for example, the reaction description provided by H. Vorbrueggen et al., Bull. Soc. Chim. Belg. 103, 453 (1994).)

Representative examples of bases suitable for use in the process of the invention include N-alkyl pyrrolidines, for example, 1,5-diazabicyclo[4.3.0]non-5-ene (DBN) and 1,8-diazabicyclo[5.4.0]dec-7-ene (DBU); guanidines, for example, N,N,N',N',N"-pentamethylguanidine; and mixtures thereof. Preferably, 1,8-diazabicyclo[5.4.0]undec-7-ene (DBU) (proton affinity of 1048 kj/mole), 1,5-diazabicyclo[4.3.0]non-5-ene (DBN) (proton affinity of 1038 kj/mole), and mixtures thereof are used in the process of the invention, as these bases provide high conversion to the desired fluorocompound, with complete inversion of configuration when a chiral alcohol is used. DBU and DBN are also readily commercially available, are liquids at room temperature, and dissolve easily in preferred reaction media. DBU is more preferred, e.g., from a cost perspective.

Generally, the process of the invention can be carried out by first combining (preferably, in a dry reaction vessel equipped with a stirring mechanism) at least one fluorinated, saturated aliphatic or alicyclic sulfonyl fluoride (a molar excess) and at least one primary or secondary alcohol. The resulting mixture is preferably protected from atmospheric moisture under a dry, inert atmosphere (for example, nitrogen) or by evacuation and sealing of the vessel. The mixture is preferably cooled (for example, using a cooling bath) to below ambient temperature (for example, a temperature in the range of about −30° C. to about 0° C., more preferably, about −20° C. to about 0° C.,), and at least one strong, aprotic, non-nucleophilic, hindered, double bond-containing, organic base is then added. The base is preferably added sufficiently slowly that a temperature below about 10° C. can be maintained. A molar excess of base (more than one equivalent (preferably, at least about 1.2 equivalents; more preferably, at least about 1.4 equivalents) per equivalent of alcohol) can be utilized to get maximal conversion of the alcohol to the desired fluorocompound. (Due to raw material cost considerations, the process of the invention is most preferably carried out using less than about 2 equivalents of both sulfonyl fluoride and base per equivalent of alcohol.)

Preferably, an inert solvent (for example, toluene, diglyme, xylene, dichloromethane, hexane, perfluorohexane, heptafluoropropyl ethyl ether, heptafluoropropyl methyl ether, 2-(trifluoromethyl)hexafluoropropyl methyl ether, 2-(trifluoromethyl)hexafluoropropyl ethyl ether, and the like, and mixtures thereof) is utilized to facilitate the mixing of the reactants, etc. Such solvent can be added to the reaction vessel at any stage of the process but is preferably added at any time prior to, or simultaneously with, the addition of base.

The reactants can be allowed to react for a short time (e.g., from 15 minutes to one hour), preferably with the cooling bath in place. Then the bath can be removed and the mixture allowed to stir for a short time (e.g., from 15 minutes to one hour). Generally, with most high boiling alcohols, the reaction can then be quenched by the addition of water to the vessel. Such addition of water generally leads to the formation of three phases: a top yellow phase comprising the desired fluorocompound dissolved in the reaction medium or solvent; a clear, colorless middle phase comprising water, unreacted base, and salt; and a brownish black bottom phase comprising salt, some solvent, and some fluorocompound product. The top organic phase can then be separated from the middle and bottom phases and the latter phases combined and re-extracted with more of the reaction solvent (or with another nonpolar organic liquid that will form a phase with water). The desired fluorocompound product can then be recovered from the combined middle and bottom phases (e.g., by re-extraction with a water-insoluble organic solvent) and acid washed (for example, with aqueous HCl) to remove salts and unreacted base. When the fluorocompound is high boiling, the solvent can then be removed in vacuo and the resulting crude product purified by, for example, fractional distillation or column chromatography. When the fluorocompound is low boiling and high boiling solvent is used, the crude product can be distilled out of the solvent and then purified by, for example, fractional distillation.

The process of the invention, which utilizes a premix of sulfonyl fluoride and alcohol, provides excellent yields over a wide range of excess amounts of base and is therefore extremely useful in an industrial setting. However, for applications where such flexibility is not necessary, it is possible to obtain improved yields relative to the prior art sulfonyl fluoride-based method (which utilizes a premix of base and alcohol and 2 to 3 equivalents of base per equivalent of alcohol) by simply limiting the amount of excess base to less than 2 equivalents. Thus, this invention further provides a selective fluorination process comprising the steps of (a) forming a mixture comprising (i) at least one primary or secondary alcohol and (ii) a molar excess of less than 2 equivalents of at least one strong, aprotic, non-nucleophilic, hindered, double bond-containing, organic base per equivalent of the alcohol; and (b) adding at least one fluorinated, saturated aliphatic or alicyclic sulfonyl fluoride to the mixture.

Objects and advantages of this invention are further illustrated by the following examples, but the particular materials and amounts thereof recited in these examples, as well as other conditions and details, should not be construed to unduly limit this invention.

EXAMPLES

In the following Examples, all temperatures are in degrees Celsius and all parts and percentages are by weight unless indicated otherwise. Commercially available materials were chemically transformed by reaction pathways well-known to those skilled in the art and detailed in the Examples. Preparations of the fluorinated alcohols used as starting materials in some of the Examples can be found in U.S. Pat. No. 5,702,637 (Kistner et al.), U.S. Pat. No. 5,474,705 (Janulis et al.), and U.S. Ser. No. 08/998,400 (Hasegawa et al.).

Compounds prepared in the various Examples of this invention were characterized by gas and liquid chromatography and by $^{19}$F-NMR spectroscopy.

Example 1
Preparation of (S)-6-(2-(2-(Nonafluorobutoxy) tetrafluoroethoxy)-2,2-difluoroethoxy)-5-fluorohex-1-ene in Methyl t-Butyl Ether A one liter flask which had been oven dried was assembled hot with an overhead stirrer, an addition funnel, and a thermocouple and was kept under positive nitrogen pressure. (R)-6-(2-(2-(Nonafluorobutoxy) tetrafluoroethoxy)-2,2-difluoroethoxy)-5-hydroxyhex-1-ene (22 g, MW=530, 0.04 mole), 19.4 g (0.06 mole) perfluorobutanesulfonyl fluoride (hereinafter, PBSF, MW=302), and 30 mL methyl t-butyl ether were added to the flask, and then the resulting mixture was cooled to 0° C. using a cooling bath. After about 5 minutes, the addition of 9.4 g DBU (MW=152, 0.060 mole) was begun. The DBU was added at such a rate that the temperature did not rise above 10° C. The cooling bath was removed, and the mixture was stirred for one hour. While stirring, 200 mL toluene and then 200 mL water were added. Three phases formed, and the top yellow toluene layer was separated as product. The toluene layer was washed three more times with water (200 mL). The toluene layer was then stripped of solvent at reduced pressure using a rotary evaporator to give 22 g of material which by gas chromatography (hereinafter, gc) analysis was found to contain 9 area % of elimination product, 88 area % of the desired (S)-6-(2-(2-(nonafluorobutoxy) tetrafluoroethoxy)-2,2-difluoroethoxy)-5-fluorohex-1-ene, and 3 area % of unreacted (R)-6-(2-(2-(nonafluorobutoxy) tetrafluoroethoxy)-2,2-difluoroethoxy)-5-hydroxyhex-1-ene.

Example 2
Preparation of (S)-6-(2-(2-(Nonafluorobutoxy) tetrafluoroethoxy)-2,2-difluoroethoxy)-5-fluorohex-1-ene in Toluene A one liter flask which had been oven dried was assembled hot with an overhead stirrer, an addition funnel, and a thermocouple and was kept under positive nitrogen pressure. (R)-6-(2-(2-(Nonafluorobutoxy) tetrafluoroethoxy)-2,2-difluoroethoxy)-5-hydroxyhex-1-ene (30 g, MW=530, 0.057 mole), PBSF (31.5 g, MW=302, 0.102 mole), and 60 mL of toluene were added to the flask, and then the resulting mixture was cooled to 0° C. using a cooling bath. After about 5 minutes, the addition of 15 g of DBU (MW=152, 0.102 mole) was begun. The DBU was added at such a rate that the temperature did not rise above 10° C. The cooling bath was removed, and the mixture was stirred for one hour. While stirring, 60 mL of toluene and then 30 mL of water were added. Three phases formed, and the top yellow toluene layer was separated as product. The toluene layer was washed with 7% aqueous HCl (60 mL). The toluene layer was then stripped of solvent at reduced pressure on a rotary evaporator to give 22 g of material which by gc analysis was found to contain 8 area % of eliminated product and 92 area % of the desired (S)-6-(2-(2-(nonafluorobutoxy)tetrafluoroethoxy)-2,2-difluoroethoxy)-5-fluorohex-1-ene.

Comparative Example 1
Use of DAST as Fluorinating Reagent

A one liter flask which had been oven dried was assembled hot with an overhead stirrer, an addition funnel, and a thermocouple and was kept under positive nitrogen pressure. (R)-6-(2-(2-(Nonafluorobutoxy) tetrafluoroethoxy)-2,2-difluoroethoxy)-5-hydroxyhex-1-ene (68 g, MW=530, 0.128 mole) was added by dropwise addition to the flask, which already contained a solution of diethylaminosulfur trifluoride (DAST, 25 g, MW=161, 0.155 mole) in methyl t-butyl ether (300 mL) at −13° C. The resulting mixture was then warmed to room temperature. The mixture was stirred at room temperature for 12 hours. The mixture was then poured into 150 mL of water. The resulting upper ether layer containing the desired product was separated and subsequently washed with 5% sodium carbonate and water. The ether was stripped in vacuo to give 65 g of crude product, which by gc analysis was found to contain 14 area % of elimination product, 85 area % of the desired (S)-6-(2-(2-(nonafluorobutoxy)tetrafluoroethoxy)-2,2-difluoroethoxy)-5-fluorohex-1-ene, and 1 area % of unreacted (R)-6-(2-(2-(nonafluorobutoxy)tetrafluoroethoxy)-2,2-difluoroethoxy)-5-hydroxyhex-1-ene. Fractional distillation through a column of steel helices at a 3/1 reflux ratio and 0.1 mm pressure gave 31.2 g of product at 91% purity.

TABLE 1

Process of Invention Compared to DAST
Fluorination of (R)-6-(2-(2-(Nonafluorobutoxy)tetrafluoroethoxy)-2,2-difluoroethoxy)-5-hydroxyhex-1-ene
$CH_2=CH(CH_2)_2CH(OH)CH_2OCH_2CF_2O(CF_2)_2OC_4F_9$
(Starting OH-Functional Compound)--→
$CH_2=CH(CH_2)_2CH(F)CH_2OCH_2CF_2O(CF_2)_2OC_4F_9$ (Desired Product)
and/or $CH_2=CH(CH_2)_2CH=CHOCH_2CF_2O(CF_2)_2OC_4F_9$ (Elimination Product)

| Example No. | Fluorinating Reagent (equivalents) | Solvent | GC Area % of Product (Elimination/Desired/OH) |
|---|---|---|---|
| C1 | DAST (1.2) | Methyl Butyl Ether | 14/85/1 |
| 1 | PBSF (1.6)/ DBU (1.6) | Methyl Butyl Ether | 9/88/3 |
| 2 | PBSF (1.8)/ DBU (1.8) | Toluene | 8/92/0 |

The data in Table 1 shows that less elimination product (relative to desired product and unreacted OH compound, as measured by gc) was obtained by using the process of the invention than was obtained by using DAST fluorination.

Examples 3–7 and Comparative Examples 2–7

Examples 3–7 and Comparative Examples 2–7 were prepared essentially as described in Example 2. Gas chromatography area % ratios were measured for the resulting crude product after stripping of solvent in vacuo.

TABLE 2

Different Bases and Solvents
$CH_2=CH(CH_2)_2CH(OH)CH_2OCH_2CF_2O(CF_2)_2OC_4F_9$ (Starting OH-
Functional Compound) + $R_fSO_2F$ + Base---→
$CH_2=CH(CH_2)_2CH(F)CH_2OCH_2CF_2O(CF_2)_2OC_4F_9$
(Desired Product) or
$CH_2=CH(CH_2)_2CH=CHOCH_2CF_2O(CF_2)_2OC_4F_9$
(Elimination Product) + $R_fSO_3^-$ Hbase$^+$
(R)-6-(2-(2-(nonafluorobutoxy)tetrafluoroethoxy)-2,2-
difluoroethoxcy)-5-hydroxyhex-1-ene →
(S)-6-(2-(2-(nonafluorobutoxy)tetrafluoroethoxy)-2,2-
difluoroethoxy)-5-fluorohex-1-ene

| Example No. | Solvent | Base (equivalents) | $R_fSO_2F$ (equivalents) | GC Area % of Product (elimination/desired/OH) | Proton Affinity (kj/mole)[8] |
|---|---|---|---|---|---|
| 3 | diglyme | DBU (1.45) | PBSF(1.46) | 13/79/8 | 1048 |
| 4 | diglyme | DBU (1.73) | PBSF(1.56) | 6/79/14 | 1048 |
| C2 | diglyme | BU$_3$N (1.73) | PBSF(1.46) | 1/19/80 | 999 |
| C3 | diglyme | (iPr)$_2$EtN (1.73) | PBSF(1.46) | 1/7/93 | 994 |
| 1 | Methyl Butyl ether | DBU (1.59) | PBSF(1.59) | 9/88/3 | 1048 |
| C4 | Methyl Butyl ether | DABCO (1.7) | PBSF(1.56) | 0/0/100 | 963 |
| 5 | diglyme | DBU (1.73) | PBSF(1.56) | 8/90/1 | 1048 |
| 6 | toluene | DBU (1.78) | PBSF(1.82) | 12/84/4 | 1048 |
| 7 | toluene | DBN (1.6) | PBSF(1.6) | 9/88/3 | 1038 |
| 2 | toluene | DBU (1.8) | PBSF(1.80) | 8/92/0 | 1048 |
| C5 | toluene | 1,8-bis-(dimethyl-amino)napthalene (1.80) | PBSF(1.8) | 0/0/100 | 1029 |
| C6 | toluene | N,N,N',N'-tetramethy 1-1,4-butanedi-amine (1.8) | PBSF(1.8) | 0/0/100 | 1036 |
| C7 | toluene | N,N,N',N'-tetramethy 1-1,3-propanedi-amine (1.8) | PBSF(1.8) | 0/0/100 | 1035 |

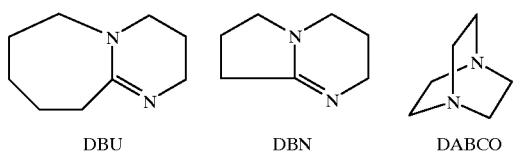

DBU          DBN          DABCO

The data in Table 2 shows the effectiveness of strong, non-nucleophilic organic amines that contain a double bond, compared with those without a double bond, as well as the usefulness of a range of solvents in the process of the invention. Comparative organic bases having lower base strengths and no double bond (for example, DABCO, 1,4-diazabicyclo[2.2.2]octane (proton affinity of 963 kj/mole, E. P. Hunter and S. G. Lias, "Proton Affinity Evaluation" in *NIST Chemistry WebBook*, NIST Standard Reference Database Number 69, Eds. W. G. Mallard and P. J. Linstrom, March 1998, National Institute of Standards and Technology, Gaithersburg, Md. 20899 (http://webbook.nist.gov)), N,N-diisopropylethyl amine (proton affinity of 994 kj/mole), and tributyl amine (proton affinity of 999 kj/mole)) provided low (or even zero) percent conversion to the desired fluorocompound and, upon aqueous workup, left unreacted alcohol. Trialkyl amines of sufficient base strength, but without a double bond (for example, N,N,N',N'-tetramethyl-1,4-butanediamine (proton affinity of 1046 kj/mole) and N,N,N',N'-tetramethyl-1,3-propanediamine (proton affinity of 1035 kj/mole)), failed to provide the desired fluorocompound product. Perfluorobutane sulfonyl fluoride (PBSF) and other perfluoroalkane sulfonyl fluorides are known to quaternize the nitrogen of the pyridine ring of strong, nucleophilic amine bases such as dimethylaminopyridine, in the presence of a hydroxyl group (e.g., see H. Vorbruggen et al., Bull. Soc. Chim. Belg. 103, 453 (1994), and U.S. Pat. No. 3,419,595 (Hansen)).

Example 8
(S)-6-(2-(2-(Nonafluorobutoxy)tetrafluoroethoxy)-2,2-difluoroethoxy)-5-fluorohex-1-ene A one liter flask that had been oven dried was assembled hot with an overhead stirrer, an addition funnel, and a thermocouple and was kept under positive nitrogen pressure. (S)-6-(2-(2-(Nonafluorobutoxy)tetrafluoroethoxy)- 2,2-difluoroethoxy)-5-hydroxyhex-1-ene (20 g, MW=530, 0.038 mole), perfluorooctanesulfonyl fluoride (POSF) (30 g, MW=502, 0.06 mole), and 40 mL toluene were added to the flask, and then the resulting mixture was cooled to 0° C. using a cooling bath. After about 5 minutes, the addition of 9.9 g DBU (MW=152, 0.065 mole) was begun. The DBU was added at such a rate that the temperature of the mixture did not rise above 10° C. The cooling bath was removed, and the mixture was stirred for one hour. While stirring, 40 ml toluene and then 100 mL water were added. Three phases formed, and the top yellow toluene phase was saved as product. The black lower phase and the clear middle phase were re-extracted with an additional 100 ml of toluene, which was combined with the previously isolated toluene phase. The toluene phase was washed three more times with water (100 ml). The toluene phase was stripped at reduced pressure on a rotary evaporator to give 14 g of crude product, which by gc was found to contain 10 area % elimination product and 88 area % desired product. The crude product was one plate distilled to give product (10.4 g, distilled at 41–42° C. at 0.03 mm) found by gc to be 92% desired product.

TABLE 3

POSF Compared With PBSF in Fluorination of
(R)-6-(2-(2-(Nonafluorobutoxy)tetrafluoroethoxy)-2,2-
difluoroethoxy)-5-hydroxyhex-1-ene

| Example Number | Solvent | Base (equivalents) | $R_fSO_2F$ (equivalents) | GC Area % (Elimination/Desired/OH) |
|---|---|---|---|---|
| 2 | Toluene | DBU (1.8) | PBSF (1.80) | 8/92/0 |
| 8 | Toluene | DBU (1.6) | POSF (1.7) | 10/90/0 |

The data in Table 3 shows that POSF is similar to PBSF in effectiveness for converting primary and secondary alcohols to the corresponding fluorides.

Example 9
(S)-8-(2-(2-(Nonafluorobutoxy)tetrafluoroethoxy)-2,2-difluoroethoxy)-7-fluorooct-1-ene A one liter flask that had been oven dried was assembled hot with an overhead stirrer, an addition funnel, and a thermocouple and was kept under positive nitrogen pressure. (R)-8-(2-(2-(Nonafluorobutoxy)tetrafluoroethoxy)-2,2-difluoroethoxy)-7-hydroxyoct-1-ene (11.3 g at 93%, MW=558, 0.0188 mole), PBSF (10.5 g, MW=302, 0.035 mole), and 30 mL toluene were added to the flask, and then the resulting mixture was cooled to 0° C. using a cooling bath. After about 5 minutes, the addition of 5.3 g DBU (MW=152, 0.035 mole) was begun. The DBU was added at such a rate that the temperature of the mixture did not rise above 10° C. The cooling bath was removed, and the mixture was stirred for one hour. While stirring, 200 mL toluene was added, then 200 ml water. Three layers formed, and the top yellow toluene layer was saved as product. The toluene layer was washed three more times with water (50 mL). The toluene layer was stripped at reduced pressure on a rotary evaporator to give 10.1 g of stripped product, which was shown by gc to be 14 area % elimination product and 86% desired product. The stripped product was one plate distilled in a Kugelrohr apparatus to give product (8.9 g, distilled at 90–110° C. at 0.01 mm) that was found by gc to be 79% desired product. The yield {100(0.79)(8.9)/10.5 (0.93)} was 67%.

Example 10

(S)-6-(2-(2-(Nonafluorobutoxy)tetrafluoroethoxy)-2,2-difluoroethoxy)-5-fluorohex-1-ene A one liter flask that had been oven dried was assembled hot with an overhead stirrer, an addition funnel, and a thermocouple and was kept under positive nitrogen pressure. (R)-8-(2-(2-(Nonafluorobutoxy)tetrafluoroethoxy)-2,2-difluoroethoxy)-5-hydroxyhex-1-ene (21.5 g at 93%, MW=530, 0.038 mole), PBSF (18 g, MW=302, 0.06 mole), and 40 mL toluene were added to the flask, and then the resulting mixture was cooled to 0° C. using a cooling bath. After about 5 minutes, the addition of 10 g DBU (MW=152, 0.066 mole) was begun. The DBU was added at such a rate that the temperature of the mixture did not rise above 10° C. The cooling bath was removed, and the mixture was stirred for one hour. While stirring, 200 mL toluene was added, then 200 mL water. Three layers formed, and the top yellow toluene layer was saved as product. The toluene layer was washed three more times with water (200 mL). The toluene layer was stripped at reduced pressure on a rotary evaporator to give 20.8 g. The stripped product was one plate distilled to give product (15.4 g, distilled at 62–70° C. at 0.3 mm) that was found by gc to be 82% desired product. NMR showed the product to be 83 weight % of the desired fluorocompound, 422OCH$_2$C(*)HF(CH$_2$)$_2$CH=CH$_2$, 6% trans-422OCH$_2$C(*)H=CHCH$_2$CH=CH$_2$, 1% cis-422OCH$_2$C(*)H=CHCH$_2$CH=CH$_2$, 8.4% 422OCH$_2$C(*)(OH)(CH$_2$)$_2$CH=CH$_2$, 3.6% trans-422OCH=CH(CH$_2$)$_2$CH=CH$_2$, 1.5% cis-4220CH=CH(CH$_2$)$_2$CH=CH$_2$. The yield {100(15.4)0.83/21.5(0.93)} was 64%.

Example 11

(S)-6-(2-(2-(Nonafluorobutoxy)tetrafluoroethoxy)-2,2-difluoroethoxy)-5-fluorohex-1-ene A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), PBSF (26.6 g, MW=302, 0.088 mole), and 40 mL toluene were added to the flask, and then the resulting mixture was cooled to 0° C. using a cooling bath. After about 5 minutes, the addition of DBU (12.8 g, MW=152, 0.084 mole) was begun. The DBU was added at such a rate that the temperature of the mixture did not rise above 10° C. The cooling bath was removed, and the mixture was stirred for one hour. While stirring, 200 mL toluene was added, then 200 mL water. Three layers formed, and the top yellow toluene layer was saved as product. The toluene layer was washed three more times with water (200 mL). The toluene layer was stripped at reduced pressure on a rotary evaporator to give 18.4 g of stripped product, which by gc was found to be 72.3 area % desired product and 6.7 area % elimination product. The stripped product was then distilled to give product (15.9 g, distilled at 62–90° C. at 0.01 mm) that was found by gc to be 83% pure. The yield {100(15.9)0.83/21.5(0.93)} was 66%.

Example 12

(S)-6-(2-(2-(Nonafluorobutoxy)tetrafluoroethoxy)-2,2-difluoroethoxy)-5-fluorohex-1-ene A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), PBSF (16 g, MW=302, 0.053 mole), and 40 mL toluene were added to the flask, and then the resulting mixture was cooled to 0° C. using a cooling bath. After about 5 minutes, the addition of DBU (15.6 g, MW=152, 0.102 mole) was begun. The DBU was added at such a rate that the temperature of the mixture did not rise above 10° C. The cooling bath was removed, and the mixture was stirred for 30 minutes. Then the mixture was sampled and found by gc to be 81% desired product and 8.3% elimination product. While stirring, 200 mL toluene was added and then 200 mL water. Three layers formed, and the top yellow toluene layer was saved as product. The toluene layer was washed three more times with water (200 mL). The toluene layer was stripped at reduced pressure on a rotary evaporator to give 18.4 g of stripped product, which was then distilled to give product (16.7 g, distilled at 45–85° C. at 0.01 mm) that was found to be 84% pure by gc. The yield {(100)16.6(0.84)/21.5(0.93)} was 70%.

Example 13

(S)-6-(2-(2-(Nonafluorobutoxy)tetrafluoroethoxy)-2,2-difluoroethoxy)-5-fluorohex-1-ene Using a Premix of Alcohol and Base (Less than 2 Equivalents of Base)

A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), DBU (6.1 g, MW=152, 0.04 mole), and 40 mL toluene were added to the flask, and then the resulting mixture was cooled to 0° C. using a cooling bath. After about 5 minutes, the addition of PBSF (17.7 g, MW=302, 0.059 mole) was begun. The PBSF was added at such a rate that the temperature of the mixture did not rise above 10° C. The cooling bath was removed, and the mixture was stirred for one hour. The mixture was sampled at this point and found by gc to be 6.5% elimination product, 76.0% desired product, and 10.9% unreacted alcohol. While stirring, 200 mL toluene was added, then 200 mL water. Three layers formed, and the top yellow toluene layer was saved as product. The toluene layer was washed three more times with water (200 mL). The toluene layer was stripped at reduced pressure on a rotary evaporator to give 20 g of stripped product, which was one plate distilled at 0.01 mm at a pot temperature of 44–85° C. to give 18.6 g of product, which by gc was found to be 76.1% desired product, 5.6% elimination product, and 9.9% unreacted alcohol. The yield {(100)18.6(0.761)/21.5(0.93) was 71%.

Example 14

(S)-6-(2-(2-(Nonafluorobutoxy)tetrafluoroethoxy)-2,2-difluoroethoxy)-5-fluorohex-1-ene Using a Premix of Alcohol and Base (Less than 2 Equivalents of Base)

A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), DBU (6.1 g, MW=152, 0.04 mole), and 40 mL toluene were added to the flask, and then the resulting mixture was cooled to 0° C. using a cooling bath. After about 5 minutes, the addition of PBSF (25.4 g, MW=302, 0.084 mole) was begun. The PBSF was added at such a rate that the temperature of the mixture did not rise above 10° C. The cooling bath was removed, and the mixture was stirred for one hour. The mixture was sampled at this point and found by gc to be 6.1% elimination product, 70% desired product, and 12.3% unreacted alcohol. While stirring, 200 mL toluene was added and then 200 mL water. Three layers formed, and the top yellow toluene layer was saved as product. The toluene layer was washed three more times with water (200 mL). The toluene layer was stripped at reduced pressure on a rotary evaporator to give 20.4 of stripped product, which was one plate distilled at 0.01 mm and 44–85° C. to give 17.2 g of product, which by gc was found to be 71% desired product, 6.2% elimination product, and 11.9% unreacted alcohol. The yield {(100)17.2(0.71)/21.5(0.93)} was 61%.

Example 15

(S)-6-(2-(2-(Nonafluorobutoxy)tetrafluoroethoxy)-2,2-difluoroethoxy)-5-fluorohex-1-ene Using a Premix of Alcohol and Base (Less than 2 Equivalents of Base)

A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), DBU (10 g, MW=152, 0.066 mole), and 40 mL toluene were added to the flask, and then the resulting mixture was cooled to 0° C. using a cooling bath. After about 5 minutes, the addition of PBSF (18 g, MW=302, 0.06 mole) was begun. The PBSF was added at such a rate that the temperature of the mixture did not rise above 10° C. The cooling bath was removed, and the mixture was stirred for one hour. While stirring, 200 mL toluene was added and then 200 mL water. Three layers formed, and the top yellow toluene layer was saved as product. The toluene layer was washed three more times with water (200 mL). The toluene layer was stripped at reduced pressure on a rotary evaporator to give 17.9 g of stripped product, which by gc was found to be 81 and 8.2 area % desired product and elimination product, respectively. The stripped product was one plate distilled to give product (15.4 g, distilled at 43–106° C. at 0.01 mm) that was found by gc to be 82% desired product. The yield {(100)15.4(0.82)/21.5(0.93)} was 63%.

Comparative Example 8

(S)-6-(2-(2-(Nonafluorobutoxy)tetrafluoroethoxy)-2,2-difluoroethoxy)-5-fluorohex-1-ene Using a Premix of Alcohol and Base (More than 2 Equivalents of Base According to the Method of U.S. Pat. No. 5,760,255 (Vorbrueggen))

A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), DBU (13 g, MW=152, 0.085 mole), and 40 mL toluene were added to the flask, and then the resulting mixture was cooled to 0° C. using a cooling bath. After about 5 minutes, the addition of PBSF (21 g, MW=302, 0.07 mole) was begun. The PBSF was added at such a rate that the temperature of the mixture did not rise above 10° C. The cooling bath was removed, and the mixture was stirred for one hour. While stirring, 200 mL toluene was added, then 200 mL water. Three layers formed, and the top yellow toluene layer was saved as product. The toluene layer was washed three more times with water (200 mL). The toluene layer was stripped at reduced pressure on a rotary evaporator to give 17.1 g of stripped product, which was then one plate distilled to give product (13.8 g, distilled at 62–70° C. at 0.05–0.3 mm) that was found by gc to be 70% desired product. The yield {(100)13.8(0.70)/21.5 (0.93)} was 48%.

Comparative Example 9

(S)-8-(2-(2-(Nonafluorobutoxy)tetrafluoroethoxy)-2,2-difluoroethoxy)-7-fluorooct-1-ene Using a Premix of Alcohol and Base (More than 2 Equivalents of Base According to the Method of U.S. Pat. No. 5,760,255 (Vorbrueggen))

A one liter flask that had been oven dried was assembled hot with an overhead stirrer, an addition funnel, and a thermocouple and was kept under positive nitrogen pressure. (R)-8-(2-(2-(Nonafluorobutoxy)tetrafluoroethoxy)-2,2-difluoroethoxy)-7-hydroxyoct-1-ene (11.3 g at 93%, MW=558, 0.020 mole), DBU (7 g, MW=152, 0.046 mole), and 30 mL toluene were added to the flask, and then the resulting mixture was cooled to 0° C. using a cooling bath. After about 5 minutes, the addition of PBSF (11.1 g, MW=302, 0.037 mole) was begun. The PBSF was added at such a rate that the temperature of the mixture did not rise above 10° C. The cooling bath was removed, and the mixture was stirred for one hour. While stirring, 200 mL toluene was added and then 200 mL water. Three layers formed, and the top yellow toluene layer was saved as product. The toluene layer was washed three more times with water (50 mL). The toluene layer was stripped at reduced pressure on a rotary evaporator to give 7.3 g of stripped product, which was then one plate distilled to give product (6.0 g, distilled at 62–70° C. at 0.03–0.3 mm) that was found by gc to be 74.5% desired product. The yield {(100)6.0(0.745)/11.3(0.93)} was 43%.

Comparative Example 10

(S)-6-(2-(2-(Nonafluorobutoxy)tetrafluoroethoxy)-2,2-difluoroethoxy)-5-fluorohex-1-ene Using a Premix of Alcohol and Base (More than 2 Equivalents of Base According to the Method of U.S. Pat. No. 5,760,255 (Vorbrueggen))

A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), DBU (15.6 g, MW=152, 0.103 mole), and 40 mL toluene were added to the flask, and then the resulting mixture was cooled to 0° C. using a cooling bath. After about 5 minutes, the addition of PBSF (16 g, MW=302, 0.053 mole) was begun. The PBSF was added at such a rate that the temperature of the mixture did not rise above 10° C. The cooling bath was removed, and the mixture was stirred for 30 minutes. Then the mixture was sampled and found by gc to be 80 area % desired product and 13.6 area % elimination product. While stirring, 200 mL toluene was added, then 200 mL water. Three layers formed, and the top yellow toluene layer was saved as product. The toluene layer was washed three more times with water (200 mL). The toluene layer was stripped at reduced pressure on a rotary evaporator to give 15.8 g of stripped product, which was then distilled to give product (15.1 g, distilled at 45–85° C. at 0.01 mm) that was found by gc to be 73.5% desired product. The yield {(100)15.1(0.735)/21.5(0.93)} was 56%.

Comparative Example 11

(S)-6-(2-(2-(Nonafluorobutoxy)tetrafluoroethoxy)-2,2-difluoroethoxy)-5-fluorohex-1-ene Using a Premix of Alcohol and Base (More than 2 Equivalents of Base According to the Method of U.S. Pat. No. 5,760,255 (Vorbrueggen))

A one liter flask that had been oven dried was assembled hot with an overhead stirrer, an addition funnel, and a thermocouple and was kept under positive nitrogen pressure. (R)-6-(2-(2-(Nonafluorobutoxy)tetrafluoroethoxy)-2,2-difluoroethoxy)-5-hydroxyhex-1-ene (21.5 g at 93%, MW=530, 0.038 mole), DBU (18.3 g, MW=152, 0.12 mole), and 40 mL toluene were added to the flask, and then the resulting mixture was cooled to 0° C. using a cooling bath. After about 5 minutes, the addition of PBSF (12.7 g, MW=302, 0.04 mole) was begun. The PBSF was added at such a rate that the temperature of the mixture did not rise above 10° C. The cooling bath was removed, and the mixture was stirred for one hour. The mixture was sampled at this point and found by gc to be 14.2% elimination product and 69% desired product. While stirring, 200 mL toluene was added, then 200 mL water. Three layers formed, and the top yellow toluene layer was saved as product. The toluene layer was washed three more times with water (200 mL). The toluene layer was stripped at reduced pressure on a rotary evaporator to give 17.8 g of stripped product, which was one plate distilled at 0.01 mm at a pot temperature of 45–92° C. to give 14.1 g of material, which by gc was found to be 69.7% desired product, 13.7% elimination product, and 6.5% unreacted alcohol. The yield {(100)14.1(0.697)/21.5 (0.93) was 49%.

Comparative Example 12

(S)-6-(2-(2-(Nonafluorobutoxy)tetrafluoroethoxy)-2,2-difluoroethoxy)-5-fluorohex-1-ene Using a Premix of Alcohol and Base (More than 2 Equivalents of Base According to the Method of U.S. Pat. No. 5,760,255 (Vorbrueggen))

A one liter flask that had been oven dried was assembled hot with an overhead stirrer, an addition funnel, and a thermocouple and was kept under positive nitrogen pressure. (R)-6-(2-(2-(nonafluorobutoxy)tetrafluoroethoxy)-2,2-difluoroethoxy)-5-hydroxyhex-1-ene (21.5 g at 93%, MW=530, 0.038 mole), DBU (18.3 g, MW=152, 0.12 mole), and 40 mL toluene were added to the flask, and then the resulting mixture was cooled to 0° C. using a cooling bath. After about 5 minutes, the addition of PBSF (25.3 g, MW=302, 0.084 mole) was begun. The PBSF was added at such a rate that the temperature of the mixture did not rise above 10° C. The cooling bath was removed, and the mixture was stirred for one hour. The mixture was sampled at this point and found by gc to be 12.8% elimination product and 71.7% desired product. While stirring, 200 mL toluene was added and then 200 mL water. Three layers formed, and the top yellow toluene layer was saved as product. The toluene layer was washed three more times with water (200 mL). The toluene layer was stripped at reduced pressure on a rotary evaporator to give 15.4 g of stripped product, which was one plate distilled at 0.01 mm and 44–92° C. to give 10.8 g of material which by gc was found to be 73.6% desired product and 12.9% elimination product. The yield {(100)10.8(0.736)/21.5(0.93)} was 40%.

TABLE 4

Comparison of Process of Invention with Method of U.S. Pat. No. 5,760,255 (Vorbrueggen)

| Example Number | Alcohol* | Premix** | DBU (equivalents) | PBSF (equivalents) | GC Area % (Elimination/ Desired) | % Yield (Desired Product on Distillation)@ |
|---|---|---|---|---|---|---|
| 9 | Alcohol 1 | Premix A | 1.86 | 1.86 | 14/86 | 67 |
| 10 | Alcohol 2 | Premix A | 1.74 | 1.57 | 7/93 | 64 |
| 11 | Alcohol 2 | Premix A | 2.2 | 2.3 | 8/92 | 66 |
| 12 | Alcohol 2 | Premix A | 2.7 | 1.4 | 9/91 | 65 |
| 13 | Alcohol 2 | Premix B | 1.05 | 1.54 | 8/92 | 71 |
| 14 | Alcohol 2 | Premix B | 1.05 | 2.21 | 8/92 | 61 |
| 15 | Alcohol 2 | Premix B | 1.74 | 1.57 | 9/91 | 63 |
| C8 | Alcohol 2 | Premix B | 2.26 | 1.84 | 22/78 | 48 |
| C9 | Alcohol 1 | Premix B | 2.3 | 1.85 | 25/75 | 42 |
| C10 | Alcohol 2 | Premix B | 2.5 | 1.26 | 15/85 | 56 |
| C11 | Alcohol 2 | Premix B | 3.16 | 1.1 | 17/83 | 49 |
| C12 | Alcohol 2 | Premix B | 3.16 | 2.2 | 15/85 | 40 |

*Alcohol 1 = (R)-8-(2-(2-(nonafluorobutoxy)tetrafluoroethoxy)-2,2-difluoroethoxy)-7-hydroxyoct-1-ene
 Alcohol 2 = (R)-6-(2-(2-(nonafluorobutoxy)tetrafluoroethoxy)-2,2-difluoroethoxy)-5-hydroxyhex-1-ene
**Premix A = Alcohol and Sulfonyl Fluoride
 Premix B = Alcohol and Base
@Yield data is on volatile fraction upon distillation, accounting for gc purity. Data does not account for losses routinely associated with purification operations such as fractional distillation or chromatography.

The data in Table 4 shows that the processes of the invention provided a reduced amount of elimination product and an increased yield of desired product, relative to the comparative process. When a premix of alcohol and sulfonyl fluoride was used, the yields of desired product were found to be surprisingly insensitive to the amount of base added.

Example 16

(S)-10-(2-(2-(Pentafluoroethoxy)tetrafluoroethoxy)-2,2-difluoroethoxy)-9-fluorodec-1-ene A one liter flask that had been oven dried was assembled hot with an overhead stirrer, an addition funnel, and a thermocouple and was kept under positive nitrogen pressure. (R)-10-(2-(2-(Pentafluoroethoxy)tetrafluoroethoxy)- 2,2-difluoroethoxy)-9-hydroxydec-1-ene (62.7 g, MW=486, 0.129 mole) and 120 mL toluene were added to the flask, and then the flask and its contents were cooled to −15° C. using a cooling bath. PBSF (69 g, MW=302, 0.226 mole) was then added to the flask. After about 5 minutes, the addition of DBU (36.7 g, MW=152, 0.239 mole) was begun. The DBU was added at such a rate that the temperature did not rise above 5° C. The cooling bath was removed, and the resulting mixture was stirred for one hour. While stirring, 120 mL toluene was added, then 120 mL water. Three layers formed, and the top yellow toluene layer was saved as product. The toluene layer was washed with 120 mL of 7% aqueous HCl. The toluene layer was stripped at reduced pressure on a rotary evaporator to give 55.9 g of stripped product, which was distilled through a 3-plate Snyder column with a splitter at 1/1 reflux ratio to give product (35.9 g, distilled at 75–77° C. at 0.03 mm) that was found by gc to be 92% desired product. The yield ((100)35.9(0.92)/62.7) was 53%.

Example 17

6-(4-(Heptafluoropropoxy)-2,2,3,3,4,4-hexafluorobutoxy)-(S)-3-fluorohexoxyprop-1-ene A one liter flask that had been oven dried was assembled hot with an overhead stirrer, an addition funnel, and a thermocouple and was kept under positive nitrogen pressure. 6-(4-(Heptafluoropropoxy)-2,2,3,3,4,4-hexafluorobutoxy)-(R)-3-hydroxyhexoxyprop-1-ene (28.6 g, MW=521, 0.055 mole) and 75 mL toluene were added to the flask, and then the flask and its contents were cooled to −15° C. using a cooling bath. PBSF (26.5 g, MW=302, 0.088 mole) was then added to the flask. After about 5 minutes, the addition of DBU (14.2 g, MW=152, 0.094 mole) was begun. The DBU was added at such a rate that the temperature did not rise above 5° C. The cooling bath was removed, and the resulting mixture was stirred for one hour. While stirring, 75 mL toluene was added, then 75 mL water. Three layers formed, and the top yellow toluene layer was saved as product. The toluene layer was washed with 75 mL of 7% aqueous HCl and then stripped at reduced pressure on a rotary evaporator. The stripped product was distilled in a Kugelrohr apparatus at 0.05 mm (oven temp 67–82° C.) to give 22 g of product found by gc to be 96% desired product. The yield ((100)22 (0.96)/28.6) was 74%.

Example 18

(S)-8-(3-(Pentafluoroethoxy)-2,2,3,3-tetrafluoropropoxy)-7-fluorooct-1-ene

A one liter flask that had been oven dried was assembled hot with an overhead stirrer, an addition funnel, and a thermocouple and was kept under positive nitrogen pressure. (R)-8-(3-(Pentafluoroethoxy)-2,2,3,3-tetrafluoropropoxy)-7-hydroxyoct-1-ene (76 g at 85% purity by gc, MW=292, 0.221 mole) and 100 mL toluene were added to the flask, and then the flask and its contents were cooled to −15° C. using a cooling bath. PBSF (91 g, MW=302, 0.301 mole) was then added to the flask. After about 5 minutes, the addition of DBU (52 g, MW=152, 0.34 mole) was begun. The DBU was added at such a rate that the temperature did not rise above 5° C. The cooling bath was removed, and the resulting mixture was stirred for one hour. While stirring, 100 mL toluene was added, then 100 mL water. Three layers formed, and the top yellow toluene layer was saved as product. The toluene layer was washed with 100 ml of 7% aqueous HCl and then stripped at reduced pressure on a rotary evaporator. The stripped product was distilled through a 3-plate Snyder column with a splitter at 1/1 reflux ratio to give product (35.0 g, distilled at 43–44° C. at 0.05 mm) that was found by gc to be 92% desired product. The yield ((100)35.0(0.92)/76 (0.85) was 50%.

Example 19

(S)-10-(2-(2-(Nonafluorobutoxy)tetrafluoroethoxy)-2,2-difluoroethoxy)-9-fluorodec-1-ene A twelve liter flask that had been baked out was assembled hot with an overhead stirrer, an addition funnel, and a thermocouple and was kept under positive nitrogen pressure. (R)-10-(2-(2-(Nonafluorobutoxy) tetrafluoroethoxy)-2,2-difluoroethoxy)-9-hydroxydec-1-ene (1754 g, MW=572, 3.07 mole) and 3300 mL toluene were added to the flask, and then the flask and its contents were cooled to −11° C. using a cooling bath. PBSF (1656 g, MW=302, 95% active, 5.20 moles, 1.70 equivalents/equivalent alcohol) was then added to the flask. After about 30 minutes, the addition of DBU (815 g, MW=152, 5.36 moles, 1.75 equivalents/equivalent alcohol) was begun. The DBU was added at such a rate that the temperature did not rise above 5° C. The cooling bath was removed, and the resulting mixture was stirred for two hours. While stirring, 1650 mL toluene was added, then 520 mL water. Three layers formed, and the top yellow toluene layer was saved as product. The black lower layer and the clear middle layer were rewashed with 520 mL water and 1650 mL toluene. The resulting upper toluene layer was saved and combined with the toluene layer from the previous phase separation. The combined toluene layer was washed with 520 mL water and then with 1566 g of 7% aqueous HCl. Subtracting the toluene peak, gc showed the material to be 87 area % of desired product and 7 area % of the byproduct formed from HF elimination. The toluene layer was stripped at reduced pressure on a rotary evaporator to give 1756 g of stripped product, which was distilled through a five plate sieve tray column to give product (1181 g, distilled at 90–98° C. at 0.03 mm) that was found by gc to be 93.7% desired product (the remainder being the by-product formed by HF elimination). The molar yield {100(1181)0.937/1756} was 63%.

Example 20

(S)-10-(3-(Pentafluoroethoxy)-2,2,3,3-tetrafluoropropoxy)-9-fluorodec-1-ene

A twelve liter flask that had been baked out was assembled hot with an overhead stirrer, an addition funnel, and a thermocouple and was kept under positive nitrogen pressure. (R)-10-(3-(Pentafluoroethoxy)-2,2,3,3-tetrafluoropropoxy)-9-hydroxydec-1-ene (1530 g, MW=420, 3.64 mole) and 2160 mL toluene were added to the flask, and then the flask and its contents were cooled to −11° C. using a cooling bath. PBSF (2100 g, MW=302, 95% active, 6.61 moles, 1.81 equivalents/equivalent alcohol) was then added to the flask. After about 30 minutes, the addition of DBU (1020 g, MW=152, 6.71 moles, 1.84 equivalents/equivalent alcohol) was begun. The DBU was added at such a rate that the temperature did not rise above 5° C. The cooling bath was removed, and the resulting mixture was stirred for two hours. While stirring, 2650 mL toluene was added, then 1500 mL water. Three layers formed, and the top yellow toluene layer was saved as product. The black lower layer and the clear middle layer were rewashed with 2650 mL toluene and 1500 mL water. The resulting upper toluene layer was saved and combined with the toluene layer from the previous phase separation. The combined toluene layer was washed with 3000 mL water and then with 3300 g of 7% aqueous HCl. Subtracting the toluene peak, gc showed the material to be 91 area % of desired product and 9 area % of the by-product formed from HF elimination. The toluene layer was stripped at reduced pressure on a rotary evaporator to give 1547 g of stripped material, which was distilled through a five plate sieve tray column to give product (995 g, distilled at 95–110° C. at 0.1 mm) that was found by gc to be 93.2% desired product (the remainder being the by-product formed by HF elimination). The molar yield {(100)993(0.932)/1560} was 61%.

Example 21

1-Benzyloxy-(S)-2-fluoro-3-(4-(pentafluoroethoxy)-2,2,3,3-tetrafluorobutoxy)propane A one liter flask that had been oven dried was assembled hot with an overhead stirrer, an addition funnel, and a thermocouple and was kept under positive nitrogen pressure. 1-Benzyloxy-(S)-2-hydroxy-3-(4-(pentafluoroethoxy)-2,2,3,3-tetrafluorobutoxy)propane (32 g, MW=480, 0.067 mole) and 75 mL toluene were added to the flask, and then the flask and its contents were cooled to −15° C. using a cooling bath. PBSF (37 g, MW=302, 0.116 mole) was then added to the flask. After about 5 minutes, the addition of DBU (18 g, MW=152, 0.118 mole) was begun. The DBU was added at such a rate that the temperature did not rise above 5° C. The cooling bath was removed, and the resulting mixture was stirred for one hour. While stirring, 75 mL toluene was added, then 75 mL water. Three layers formed, and the top yellow toluene layer was saved as product. The toluene layer was washed with 75 mL of 7% aqueous HCl and then stripped at reduced pressure on a rotary evaporator to give 28 g of stripped product, found by gc to be 93 area % desired product. The stripped product was distilled to give product (20.8 g, distilled at 75–85° C. at 0.03 mm) that was found by gc to be 92% desired product. The yield {(100)20.8(0.92)/32} was 60%.

Example 22

5-Octyl-2-[4-((S)-2-fluoro-3-(2-(2-(nonafluorobutoxy)tetrafluoroethoxy)-2,2-difluoroethoxy)propoxy)phenyl]pyrimidine from 5-Octyl-2-[4-((R)-2-hydroxy-3-(2-(2-(nonafluorobutoxy)tetrafluoroethoxy)-2,2-difluoroethoxy)propoxy)phenyl]pyrimidine A one liter flask that had been oven dried was assembled hot with an overhead stirrer, an addition funnel, and a thermocouple and was kept under positive nitrogen pressure. 5-Octyl-2-[4-((R)-2-hydroxy-3-(2-(2-(nonafluorobutoxy)tetrafluoroethoxy)-2,2-difluoroethoxy)propoxy)phenyl]pyrimidine (5 g, MW=756, 0.0066 mole) and 20 mL toluene were added to the flask, and then the flask and its contents were cooled to −15° C. using a cooling bath. PBSF (3.2 g, MW=302, 0.010 mole) was then added to the flask. After about 5 minutes, the addition of DBU (1.7 g, MW=152, 0.011 mole) was begun. The DBU was added at such a rate that the temperature did not rise above 5° C. The cooling bath was removed, and the resulting mixture was stirred for one hour. While stirring, 100 mL toluene was added, then 100 mL water. Two layers formed, and the top yellow toluene layer was saved as product. The toluene layer was washed with 100 mL of 7% aqueous HCl, then with 100 mL water, followed by 100 mL water. The toluene layer was stripped at reduced pressure on a rotary evaporator to give 5.2 g of stripped product. A thin layer chromatograph of the stripped product using 10% ethyl acetate/toluene showed no starting alcohol. The stripped product was distilled in a Kugelrohr apparatus at 0.05–0.1 mm (oven temp 193–210° C.) to give 3.6 g of product, which NMR showed to be 90% desired product, 1.2% starting alcohol, 1.7% elimination product, and the remainder to be the phenol (C-phenyl pyrimidine phenol). The yield {(100)3.6(0.90)/5.0} was 65%.

Example 23

(R)-Benzyloxy(5-fluoroheptane) $CH_3CH_2C(*)H(F)(CH_2)_4OCH_2C_6H_5$ (R)-6-Benzyloxyhex-1-ene oxide was prepared by copper catalyzed addition of 3-benzyloxypropyl-1-magnesium bromide to R-epichlorohydrin to form R-1-chloro-6-benzyloxyhexan-2-ol, which was then ring closed under basic conditions to (R)-6-benzyloxyhex-1-ene oxide. This epoxide was then treated with methyl lithium (1.5 M in diethyl ether) in the presence of dilithiotetrachlorocuprate (0.02 molar equivalents, 0.1 M in tetrahydrofuran) to yield (S)-1-benzyloxy-5-hydroxyheptane.

A one liter flask that had been oven dried was assembled hot with an overhead stirrer, an addition funnel, and a thermocouple and was kept under positive nitrogen pressure. (S)-1-Benzyloxy-5-hydroxyheptane (11 g, 0.0495 mole) and 140 mL toluene were added to the flask, and then the flask and its contents were cooled to −15° C. using a cooling bath. PBSF (26.3 g, MW=302, 0.0871 mole) was then added to the flask. After about 5 minutes, the addition of DBU (14 g, MW=152, 0.0921 mole) was begun. The DBU was added at such a rate that the temperature did not rise above 5° C. The cooling bath was removed, and the resulting mixture was stirred for one hour. While stirring, 140 mL toluene was added, then 100 mL water. Two layers formed, and the top yellow toluene layer was saved as product. The toluene layer was washed with 100 mL of 7% aqueous HCl, then with 100 mL water, followed by 100 mL water. The toluene layer was stripped at reduced pressure on a rotary evaporator to give 11.3 g of gold-colored liquid which by gc was determined to be 84% desired product and 13% elimination (olefin) product. The stripped product was chromatographed on silica gel with 40:1 hexane/ethyl acetate (volume ratio) to give 6.05 g of clear liquid. H-NMR showed this clear liquid to be 95% desired product, 0.4% $RCH_2F$, 1.4% $RCH_2CF_2CF_2CF_2F$, and 3% ethyl ether (mole %).

Example 24

(R)-Benzyloxy(5-fluorooctane) $CH_3CH_2CH_2C(*)H(F)(CH_2)_4OCH_2C_6H_5$ (R)-6-Benzyloxyhex-1-ene oxide was prepared by copper catalyzed addition of 3-benzyloxypropyl-1-magnesium bromide to R-epichlorohydrin to form R-1-chloro-6-benzyloxyhexan-2-ol, which was then ring closed under basic conditions to (R)-6-benzyloxyhex-1-ene oxide. This epoxide was then treated with ethyl magnesium bromide (1.5 M in diethyl ether) in the presence of dilithiotetrachlorocuprate (0.02 molar equivalents, 0.1 M in tetrahydrofuran) to yield (S)-1-benzyloxy-5-hydroxyoctane.

A one liter flask that had been oven dried was assembled hot with an overhead stirrer, an addition funnel, and a thermocouple and was kept under positive nitrogen pressure. (S)-1-Benzyloxy-5-hydroxyoctane (22 g, 0.093 mole) and 250 mL toluene were added to the flask, and then the flask and its contents were cooled to −15° C. using a cooling bath. PBSF (49.5 g, MW=302, 0.163 mole) was then added to the flask. After about 5 minutes, the addition of DBU (26 g, MW=152, 0.173 mole) was begun. The DBU was added at such a rate that the temperature did not rise above 5° C. The cooling bath was removed, and the resulting mixture was stirred for one hour. While stirring, 250 mL toluene was added, then 100 mL water. Two layers formed, and the top yellow toluene layer was saved as product. The toluene layer was washed with 100 mL of 7% aqueous HCl, then with 100 mL water, followed by 100 mL water. The toluene layer was stripped at reduced pressure on a rotary evaporator to give 22.9 g of gold-colored liquid, which by gc was determined to be 83% desired product and 16% elimination (olefin)

product. The stripped product was chromatograghed on silica gel with 40:1 hexane/ethyl acetate (volume ratio) to give 12.7 g of clear liquid. H-NMR showed this clear liquid to be 97% desired product, 0.4% RCH$_2$F, and 1.4% RCH$_2$CF$_2$CF$_2$CF$_2$F (mole %).

Example 25

(R)-Benzyloxy(5-fluorohexane) CH$_3$C(*)H(F)(CH$_2$)$_4$OCH$_2$C$_6$H$_5$ (R)-6-Benzyloxyhex-1-ene oxide was prepared by copper catalyzed addition of 3-benzyloxypropyl-1-magnesium bromide to (R)-epichlorohydrin to form (R)-1-chloro-6-benzyloxyhexan-2-ol, which was then dehydrated under basic conditions to (R)-6-benzyloxyhex-1-ene oxide. This intermediate epoxide was reduced with lithium triethyl borohydride to yield (S)-1-benzyloxy-5-hydroxyhexane.

A one liter flask that had been oven dried was assembled hot with an overhead stirrer, an addition funnel, and a thermocouple and was kept under positive nitrogen pressure. (S)-1-benzyloxy-5-hydroxyhexane (12 g, 0.0576 mole) and 150 mL toluene were added to the flask, and then the flask and its contents were cooled to –15° C. using a cooling bath. PBSF (30.6 g, MW=302, 0.101 mole) was then added to the flask. After about 5 minutes, the addition of DBU (16 g, MW=152, 0.107 mole) was begun. The DBU was added at such a rate that the temperature did not rise above 5° C. The cooling bath was removed, and the resulting mixture was stirred for one hour. While stirring, 150 mL toluene was added, then 100 mL water. Two layers formed, and the top yellow toluene layer was saved as product. The toluene layer was washed with 100 mL of 7% aqueous HCl, then with 100 mL water, followed by 100 mL water. The toluene layer was stripped at reduced pressure on a rotary evaporator to give 11.3 g of gold-colored liquid, which by gc was determined to be 78% desired product and 22% elimination (olefin) product. The stripped product was chromatograghed on silica gel with 40:1 (by volume) hexane/ethyl acetate (volume ratio) to give 4.7 g of clear liquid. H-NMR showed this clear liquid to be 95% desired product, 0.5% RCH$_2$CF$_2$CF$_2$CF$_2$F, 1% RCH$_2$F, and 3% ethyl ether (mole %).

Example 26

(R)-6-Fluorooctene C$_2$H$_5$C(*)H((F)(CH$_2$)$_3$CH=CH$_2$ (R)-6-chloro-5-hydroxy-heptene was prepared by copper catalyzed addition of the Grignard of 4-bromobutene with (R)-epichlorohydrin. Into a dry 1 liter flask under positive nitrogen pressure was placed 400 mL of dry tetrahydrofuran (THF) and 10.8 g of NaH (60% in oil, 269 mmoles). The flask was cooled to –10° C., and 40 g (269 mmoles) of R-6-chloro-5-hydroxyheptene was added slowly over a 30 minute period. The reaction mixture was stirred for 90 minutes at –10° C., before cooling the mixture to –70° C. At this time, 54 mL of 0.1M CuLi$_2$Cl$_4$ in THF (5 mmoles) and 296 mL of 1.0M methylmagnesium bromide in butyl ether were added. The resulting mixture was stirred at –70° C. for one hour and then allowed to warm to 0° C. The reaction was quenched with saturated ammonium chloride and the mixture stirred overnight. The resulting upper organic layer was separated off, and the remaining water layer was extracted with ethyl ether. Both organic phases were combined and stripped under reduced pressure. The residue was distilled at atmospheric pressure to give 20 g of material, which was 100% desired (S)-6-hydroxyoctene by gc.

A 100 mL flask that had been oven dried was assembled hot with a magnetic stirrer, an addition funnel, and a thermocouple and was kept under positive nitrogen pressure. (S)-6-Hydroxyoctene (20 g, 0.156 mole) and 250 mL tetraglyme (tetraethyleneglycol dimethyl ether) were added to the flask, and then the flask and its contents were cooled to –15° C. using a cooling bath. PBSF (84.6 g, MW=302, 0.280 mole) was then added to the flask. After about 5 minutes, the addition of DBU (45.7 g, MW=152, 0.300 mole) was begun. The DBU was added at such a rate that the temperature did not rise above 5° C. The cooling bath was removed, and the resulting mixture was stirred for two hours. Using a short path distillation apparatus, the product was distilled directly out of the mixture at 1.5 mm vacuum into a dry ice trap. A total of 11.0 g material was obtained, which gc showed to be 91% desired product. The yield {(100)11.0(0.91)/20} was 50%.

Example 27

Chirality of (S)-5-hexyloxy-2-[4-(6-(2-(2-(nonafluorobutoxy)tetrafluoroethoxy)-2,2-difluoroethoxy)-5-fluorohexyl)phenyl]pyrimidine In a ferroelectric liquid crystal, the polarization and the switching are due to the chirality of the compounds). A loss in chirality leads to lower polarizations and longer switching times (Tau). In this example, the polarization and switching of (S)-5-hexyloxy-2-[4-(6-(2-(2-(nonafluorobutoxy)tetrafluoroethoxy)-2,2-difluoroethoxy)-5-fluorohexyl)phenyl]pyrimidine, [C$_6$H$_{13}$O-(pyrimidineC$_4$H$_2$N$_2$)—C$_6$H$_4$—CH$_2$CH$_2$(CH$_2$)$_2$CH(F)CH$_2$OCH$_2$CF$_2$O(CF$_2$)$_2$OC$_4$F$_9$], prepare process of the invention (Example 1) were compared with the polarization and switching of the same compound prepared using DAST fluorination (Comparative Example 1). The same sign (+ or –) and the same values of the polarization and the switching (Tau), within experimental error, were observed at several different temperatures as shown below in Table 5. This indicated that no loss in chirality occurred when the process of the present invention was used. As in DAST fluorination, the process of the invention was observed to maintain the enantiomeric purity of the chiral alcohol, with complete inversion of configuration.

TABLE 5

Polarization and Switching of Fluorides Prepared by DAST Fluorination and by the Process of the Invention

| Temperature, T-T$_c$ (° C.)* | DAST Fluorination: Polarization (nC/cm$^2$) | Process of the Invention: Polarization (nC/cm$^2$) | DAST Fluorination: Tau (μsec) | Process of the Invention: Tau (μsec) |
| --- | --- | --- | --- | --- |
| 10 | 36.2 | 35.2 | 5.2 | 4.95 |
| 30 | 52.2 | 49.5 | 7.0 | 6.42 |
| 50 | 62.3 | 60.9 | 9.6 | 9.8 |

*where T$_c$ is the smectic A to smectic C transition temperature and T is the temperature of the measurement.

The polarization was determined essentially as described by Miyasato et al. in Jap. J. Appl. Phys. 22, 661 (1983). The electronic response time, $\tau_{electric}$ (Tau), was derived from the displacement current of the ferroelectric liquid crystal device under an applied square voltage pulse. The current was viewed on a 100 megahertz bandwidth oscilloscope. The usual decaying exponential, associated with a dielectric filled capacitor, was followed by the spontaneous polarization (P$_s$) switching pulse. The time from the rising edge of the voltage pulse to the peak of the P$_s$ pulse was taken to be $\tau_{electric}$.

Various modifications and alterations of this invention will become apparent to those skilled in the art without departing from the scope and spirit of this invention.

What is claimed is:

1. A process for preparing a fluoride from its corresponding alcohol comprising the steps of (a) forming a mixture comprising (i) at least one fluorinated, saturated aliphatic or alicyclic sulfonyl fluoride and (ii) at least one primary or secondary alcohol; and (b) adding a molar excess of at least one strong, aprotic, non-nucleophilic, hindered, double bond-containing, organic base to said mixture.

2. The process of claim 1 further comprising the step of cooling said mixture to a temperature in the range of about −30° C. to about 0° C. before adding said base.

3. The process of claim 1 wherein said sulfonyl fluoride is represented by the general formula $R_fSO_2F$, where $R_f$ is selected from the group consisting of perfluorinated alkyl groups having from 1 to about 10 carbon atoms; partially-fluorinated alkyl groups having from 1 to about 10 carbon atoms; unsubstituted or perfluoroalkyl-substituted, perfluorinated cycloalkyl groups having from about 4 to about 8 carbon atoms; and unsubstituted or perfluoroalkyl-substituted, partially-fluorinated cycloalkyl groups having from about 4 to about 8 carbon atoms.

4. The process of claim 3 wherein said $R_f$ is a perfluorinated alkyl group having from 1 to about 10 carbon atoms.

5. The process of claim 1 wherein said sulfonyl fluoride is selected from the group consisting of $CF_3SO_2F$, $C_2F_5SO_2F$, $C_4F_9SO_2F$, $C_6F_{13}SO_2F$, $C_8F_{17}SO_2F$, $C_{10}F_{21}SO_2F$, cyclo-$(C_6F_{11})SO_2F$, $C_2F_5$-cyclo-$(C_6F_{10})$ $SO_2F$, $H(CF_2)_4SO_2F$, $H(CF_2)_8SO_2F$, and mixtures thereof.

6. The process of claim 5 wherein said sulfonyl fluoride is selected from the group consisting of perfluorobutanesulfonyl fluoride, perfluorohexanesulfonyl fluoride, perfluorooctanesulfonyl fluoride, and mixtures thereof.

7. The process of claim 6 wherein said sulfonyl fluoride is perfluorobutanesulfonyl fluoride.

8. The process of claim 1 wherein said alcohol is represented by the general formula $R_1R_2CH$—OH where $R_1$ and $R_2$ are independently selected from the group consisting of branched or linear aliphatic groups, alicyclic groups, araliphatic groups, aromatic groups, hydrogen, branched or linear fluoroaliphatic groups, fluoroalicyclic groups, fluoroaraliphatic groups, and fluoroaromatic groups; wherein said aliphatic, alicyclic, araliphatic, fluoroaliphatic, fluoroalicyclic, and fluoroaraliphatic groups can contain catenary heteroatoms and/or one or two olefinic double bonds.

9. The process of claim 8 wherein said $R_1$ and $R_2$ are independently selected from the group consisting of branched or linear aliphatic groups, branched or linear fluoroaliphatic groups, araliphatic groups, and alicyclic groups.

10. The process of claim 9 wherein said $R_1$ and $R_2$ are independently selected from the group consisting of branched or linear aliphatic groups, branched or linear fluoroaliphatic groups, and araliphatic groups.

11. The process of claim 8 wherein said fluoroaliphatic groups comprise a moiety that is represented by the formula —D—$R_f'$, where D is selected from the group consisting of a covalent bond, —O—, —$OC_rH_{2r}$—, —$O(C_rH_{2r}O)_t$—$C_rH_{2r}$—, —$C_rH_{2r}$—, and —$(C_rH_{2r}O)_t$—$C_rH_{2r}$—, where r is an integer of 1 to about 20 and t is an integer of 1 to about 6; and $R_f'$ is selected from the group consisting of —$(C_xF_{2x}O)_zC_yF_{2y+1}$ and —$C_qF_{2q}X$, where x is independently an integer of 1 to about 10 for each $C_xF_{2x}O$ group, y is an integer of 1 to about 10, z is an integer of 1 to about 10, q is an integer of 1 to about 15, and X is selected from the group consisting of hydrogen and fluorine.

12. The process of claim 1 wherein said alcohol is selected from the group consisting of $CH_3CHOHCH(CH_3)_2$,
$C_6H_{11}OH$,
$C_6F_{11}CHOHCH_3$,
$C_6H_5CH_2CH_2OH$,
$C_6H_5CH_2CH_2CH_2OH$,
$C_6H_5CHOHC_6H_5$,
$C_6F_5CHOHC_6H_5$,
$CH_3OCOCH_2CHOHCH_2CH_3$,
$C_{10}H_{11}OH$(1,2,3,4-tetrahydro-2-hydroxynaphthalene),
$CH_2=CH(CH_2)_nCH(OH)CH_2OCH_2$—$(C_xF_{2x}O)_zC_yF_{2y+1}$,
$C_6H_5CH_2O(CH_2)_nCH(OH)CH_2$—$(C_xF_{2x}O)_zC_yF_{2y+1}$,
$CH_3C(=O)O(CH_2)_nCH(OH)CH_2OCH_2$—$(C_xF_{2x}O)_zC_yF_{2y+1}$,
THP—$O(CH_2)_nCH(OH)CH_2OCH_2$—$(C_xF_{2x}O)_zC_yF_{2y+1}$,
$C_8H_{17}$—$C_4H_2N_2$—$C_6H_4O(CH_2)_nCH(OH)CH_2OCH_2(C_xF_{2x}O)_zC_yF_{2y+1}$,
$C_7H_{15}$—$C_4H_2N_2$—$C_6H_4O(CH_2)_nCH(OH)CH_2OCH_2(C_xF_{2x}O)_zC_yF_{2y+1}$,
$C_6H_{13}$—$C_4H_2N_2$—$C_6H_4O(CH_2)_nCH(OH)CH_2OCH_2(C_xF_{2x}O)_zC_yF_{2y+1}$,
$C_8H_{17}O$—$C_4H_2N_2$—$C_6H_4O(CH_2)_nCH(OH)CH_2OCH_2(C_xF_{2x}O)_zC_yF_{2y+1}$,
$C_7H_{15}O$—$C_4H_2N_2$—$C_6H_4O(CH_2)_nCH(OH)CH_2OCH_2(C_xF_{2x}O)_zC_yF_{2y+1}$,
$C_6H_{13}O$—$C_4H_2N_2$—$C_6H_4O(CH_2)_nCH(OH)CH_2OCH_2(C_xF_{2x}O)_zC_yF_{2y+1}$,
$CH_3(CH_2)_bCH(OH)(CH_2)_mCH=CH_2$,
$CH_3(CH_2)_bCH(OH)(CH_2)_mOC(=O)CH_3$, $CH_3(CH_2)_bCH(OH)(CH_2)_mO$—THP,
$CH_3(CH_2)_bCH(OH)(CH_2)_mOCH_2C_6H_5$, 16alpha-hydroxyestone, 3beta-hydroxycholestan, 3alpha-andostan, 16beta-hydroxy-3-[[(trifluoromethyl)sulfonyl]oxy]esta-1,3,5(10)-trien-17-one, thymidine, 5'-deoxythymidine, uridine, 2'-deoxyuridine, 2'-deoxy-5-(trifluoromethyl)uridine, guanosine, 2'-deoxyguanosine, adenosine, 2'-desoxyadensoine, 5'-deoxyadenosine, and mixtures thereof, where x is independently an integer of 1 to about 10 for each $C_xF_{2x}O$ group, y is an integer of 1 to about 10, and z is an integer of 1 to about 10, where n and m are independently integers of one to about ten, b is an integer of zero to about 10, and THP= tetrahydropyranyl.

13. The process of claim 1 wherein said alcohol is selected from the group consisting of $CH_2=CH(CH_2)_2CH(OH)CH_2OCH_2CF_2OCF_2CF_2OC_4F_9$,
$C_6H_5CH_2O(CH_2)_2CH(OH)CH_2OCH_2CF_2OCF_2CF_2OC_4F_9$,
$CH_3C(=O)O(CH_2)_2CH(OH)CH_2OCH_2CF_2OCF_2CF_2OC_4F_9$,
THP—$OCH_2CH(OH)CH_2OCH_2CF_2OCF_2CF_2OC_4F_9$,
$CH_2=CH(CH_2)_2CH(OH)CH_2OCH_2CF_2O(CF_2CF_2O)_2CF_3$,
$CH_3C(=O)O(CH_2)_2CH(OH)CH_2CH_2OCH_2CF_2O(CF_2CF_2O)_2CF_3$,
$C_6H_5CH_2O(CH_2)_2CH(OH)CH_2CH_2OCH_2CF_2O(CF_2CF_2O)_2 CF_3$,
THP—$O(CH_2)_2CH(OH)CH_2CH_2OCH_2CF_2O(CF_2CF_2O)_2CF_3$,
$CH_2=CH(CH_2)_2CH(OH)CH_2OCH_2CF_2CF_2OC_2F_5$,
$C_6H_5CH_2O(CH_2)_2CH(OH)CH_2OCH_2CF_2CF_2OC_2F_5$,
$CH_3C(=O)O(CH_2)_2CH(OH)CH_2OCH_2CF_2CF_2OC_2F_5$,
THP—$O(CH_2)_2CH(OH)CH_2OCH_2CF_2CF_2OC_2F_5$,
$C_6H_5CH_2O(CH_2)_2CH(OH)CH_2OCH_2C_7F_{15}$,
$C_6H_5CH_2O(CH_2)_2CH(OH)CH_2OCH_2C_3F_7$,
$C_8H_{17}$—$C_4H_2N_2$—$C_6H_4OCH_2CH(OH)CH_2OCH_2CF_2OCF_2CF_2OC_4f_9$,
$C_8H_{17}$—$C_4H_2N_2$—$C_6H_4OCH_2CH(OH)CH_2OCH_2CF_2O(CF_2CF_2O)_2CF_3$,
$C_8H_{17}O$—$C_4H_2N_2$—$C_6H_4OCH_2CH(OH)CH_2OCH_2CF_2CF_2OC_2F_5$, $C_8H_{17}$—$C_4H_2N_2$—$C_6H_4OCH_2CH(OH)CH_2OCH_2C_7F_{15}$, $CH_3CH(OH)(CH_2)_4OCH_2C_6H_5$, $CH_3CH_2CH(OH)(CH_2)_4OCH_2C_6H_5$, $CH_3CH_2CH_2CH(OH)(CH_2)_4OCH_2C_6H_5$, $CH_3(CH_2)_3CH(OH)(CH_2)_4OCH_2C_6H_5$, $CH_3CH_2CH(OH)(CH_2)_3CH=CH_2$, and mixtures thereof, where THP= tetrahydropyranyl.

14. The process of claim 1 wherein said alcohol is chiral or racemic.

15. The process of claim 14 wherein said alcohol is chiral.

16. The process of claim 1 wherein said base is capable of enabling the formation of a sulfonate ester without substantially inducing elimination.

17. The process of claim 16 wherein said base exhibits a gas phase proton affinity of at least about 1000 kJ/mole.

18. The process of claim 1 wherein said base is selected from the group consisting of N-alkyl pyrrolidines, guanidines, and mixtures thereof.

19. The process of claim 18 wherein said N-alkyl pyrrolidines are selected from the group consisting of 1,5-diazabicyclo[4.3.0]non-5-ene (DBN) and 1,8-diazabicyclo[5.4.0]dec-7-ene (DBU); and said guanidine is N,N,N',N',N"-pentamethylguanidine.

20. The process of claim 19 wherein said base is selected from the group consisting of 1,8-diazabicyclo[5.4.0]undec-7-ene (DBU), 1,5-diazabicyclo[4.3.0]non-5-ene (DBN), and mixtures thereof.

21. The process of claim 20 wherein said base is 1,8-diazabicyclo[5.4.0]undec-7-ene (DBU).

22. The process of claim 1 wherein said molar excess is at least about 1.2 equivalents per equivalent of alcohol.

23. The process of claim 1 wherein said process is carried out using less than about 2 equivalents of both sulfonyl fluoride and base per equivalent of alcohol.

24. The process of claim 1 wherein said base is added sufficiently slowly that said mixture is maintained at a temperature below about 10° C.

25. The process of claim 1 further comprising the step of adding at least one inert solvent.

26. The process of claim 1 further comprising the step of recovering the resulting fluoride product.

27. A process for preparing a fluoride from its corresponding alcohol comprising the steps of (a) forming a mixture comprising (i) a sulfonyl fluoride represented by the general formula $R_fSO_2F$, where $R_f$ is a perfluorinated alkyl group having from 1 to about 10 carbon atoms and (ii) at least one primary or secondary alcohol represented by the general formula $R_1R_2CH$—OH where $R_1$ and $R_2$ are independently selected from the group consisting of branched or linear aliphatic groups, alicyclic groups, araliphatic groups, aromatic groups, hydrogen, branched or linear fluoroaliphatic groups, fluoroalicyclic groups, fluoroaraliphatic groups, and fluoroaromatic groups, wherein said aliphatic, alicyclic, araliphatic, fluoroaliphatic, fluoroalicyclic, and fluoroaraliphatic groups can contain catenary heteroatoms and/or one or two olefinic double bonds; and (b) adding to said mixture a molar excess of a strong, aprotic, non-nucleophilic, hindered, double bond-containing, organic base selected from the group consisting of N-alkyl pyrrolidines, guanidines, and mixtures thereof.

28. A process for preparing a fluoride from its corresponding alcohol comprising the steps of (a) forming a mixture comprising (i) at least one primary or secondary alcohol and (ii) a molar excess of at least one strong, aprotic, non-nucleophilic, hindered, double bond-containing, organic base, said molar excess being less than 2 equivalents of said base per equivalent of said alcohol; and (b) adding at least one fluorinated, saturated aliphatic or alicyclic sulfonyl fluoride to said mixture.

* * * * *

UNITED STATES PATENT AND TRADEMARK OFFICE
CERTIFICATE OF CORRECTION

PATENT NO. : 6,248,889 B1
DATED : June 19, 2001
INVENTOR(S) : Patricia M. Savu and Daniel C. Snustad It is certified that error appears in the above-identified patent and that said Letters Patent is hereby corrected as shown below:

Column 4,
Line 15, "$CH_2 = CH\ CH_2$)" should read -- $CH_2 = CH\ (CH_2)$ --.
Line 26, "$C_9$" should read -- $C_8$ --.

Column 22,
Line 26, "prepare process" should read -- prepared by the process --.

Column 24,
Line 5, "$C_6H_5CH_2CH_2CH_2OH$", should read -- $C_6F_5\ CH_2CH_2CH_2OH$ --.
Line 63, "$f_9$", should read -- $F_9$ --.

Signed and Sealed this

Fourth Day of June, 2002

Attest:

Attesting Officer

JAMES E. ROGAN
Director of the United States Patent and Trademark Office